(12) United States Patent
Feaster et al.

(10) Patent No.: US 7,390,674 B2
(45) Date of Patent: Jun. 24, 2008

(54) LATERAL FLOW DEVICES USING REACTIVE CHEMISTRY

(75) Inventors: Shawn Ray Feaster, Duluth, GA (US); Kaiyuan Yang, Cumming, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 409 days.

(21) Appl. No.: 11/079,730

(22) Filed: Mar. 14, 2005

(65) Prior Publication Data

US 2006/0205087 A1    Sep. 14, 2006

(51) Int. Cl.
*G01N 33/53* (2006.01)

(52) U.S. Cl. .................. 436/514; 435/287.1; 435/287.2; 435/287.7; 435/287.9; 435/970; 435/805; 435/810; 436/518; 436/164; 436/169; 436/524; 436/529; 436/805; 436/810; 422/56; 422/60

(58) Field of Classification Search .............. 435/287.1, 435/287.2, 287.7, 287.9, 970, 805, 810; 436/518, 436/514, 164, 169, 524, 529, 805, 810; 422/56–68
See application file for complete search history.

(56) References Cited

U.S. PATENT DOCUMENTS

| | | | |
|---|---|---|---|
| 4,391,904 A * | 7/1983 | Litman et al. .............. | 435/7.91 |
| 4,973,549 A | 11/1990 | Khanna et al. | |
| 5,620,863 A | 4/1997 | Tomasco et al. | |
| 5,728,587 A * | 3/1998 | Kang et al. .................. | 436/518 |
| 6,350,543 B2 | 2/2002 | Yang et al. | |
| 6,436,651 B1 | 8/2002 | Everhart et al. | |
| 6,797,481 B1 * | 9/2004 | Ullman et al. ................ | 435/7.1 |
| 2003/0045003 A1 | 3/2003 | Smith | |
| 2003/0235923 A1 | 12/2003 | Jurik et al. | |
| 2005/0191704 A1 * | 9/2005 | Boga et al. .................... | 435/7.1 |

FOREIGN PATENT DOCUMENTS

| | | |
|---|---|---|
| DE | 224950 | 7/1985 |
| DE | 19845771 | 3/2000 |
| EP | 0339331 A2 | 11/1989 |
| EP | 1130395 A2 | 9/2001 |

OTHER PUBLICATIONS

Patent Abstracts of Japan, Publication No. JP 05003799, Jan. 14, 1993.

(Continued)

*Primary Examiner*—Bao-Thuy L Nguyen
(74) *Attorney, Agent, or Firm*—Vincent T. Kung; Nancy M. Klembus; James B. Robinson

(57) ABSTRACT

There is provided a lateral flow assay device for detecting the presence or quantity of an analyte residing in a test sample where the lateral flow assay device has a porous membrane in communication with a wicking pad. The porous membrane has a detection zone which has a chromophore configured to chemically react with an analyte or a secondary trigger or a reaction product from the analyte and a trigger generating reagent(s), to generate a visually detectible signal. Additional chrmophore zones may be located downstream from the first chrmophore zone to generate signals of varying color. Scavenging zones may be included between chromophore zones to attenuate the signal by reacting with the analyte without generating a visually detectable signal.

5 Claims, 2 Drawing Sheets

OTHER PUBLICATIONS

Rahman, A.F.M.M. et al., "The First Sideways-Bonded Peroxo Complex for a Tetraaminecobalt(III) Species," *Inorganic Chemistry*, vol. 43, No. 24, 2004, pp. 7558-7560.

"Troubleshooting protein bind nitrocellulose membranes," Internet web page, http://www.devicelink.com/ivdt/archive/99/09/002.html, viewed and printed Jan. 28, 2005, pp. 1-15.

* cited by examiner

LATERAL FLOW DEVICES USING REACTIVE CHEMISTRY

BACKGROUND OF THE INVENTION

This invention concerns the use of lateral flow devices in the detection of analyte levels.

Flow through or lateral-flow assays have become more common for many analytes. These devices works on the principal of capillary flow of a mobile phase like a bodily fluid, through a porous solid support membrane. Traditional lateral flow tests use dyed or metallic nanoparticles that become entrapped or bound within pre-defined binding sites in the presence of the analyte of interest. Increasing concentrations of analyte produce increasing densities of nanoparticles within these binding sites. The amount of analyte may therefore be determined by quantifying the number of nanoparticles. This has generally necessitated the use of a reader, adding both to the complexity and to the cost of the test.

There remains a need for a rapid, quantitative test that obviates the need for a reader.

SUMMARY OF THE INVENTION

In accordance with one embodiment of the present invention, an assay device for detecting the presence or quantity of an analyte residing in a test sample is disclosed. The assay device includes a bibulous membrane in which a plurality of zones of a chromophore, specific to an analyte trigger which can be the analyte itself or a secondary trigger or a reaction product from the analyte and a trigger generating reagent(s), are immobilized in a precise pattern. Each of these chromophore zones is designed to appear in an all or none fashion by tailoring the reactivity or response of the chromophore to that of a trigger. The chromophores undergo a visually perceptible transformation, and by increasing the number of zones, one can encode any desired quantitiy or range of trigger concentrations.

The zones need not contain the same chromophore. If, for example, it is desired to convey that the analyte level is within the acceptable, borderline or high range the chromophores in succeeding zones may produce green, yellow and red colors, respectively.

Scavenging zones may be interspersed between reactive zones if desired. These scavenging zones contain reactants that react with the trigger but produce no visual change, thereby effectively attenuating the amount of trigger in the sample.

Other features and aspects of the present invention are discussed in greater detail below.

DETAILED DESCRIPTION

Figure 1:
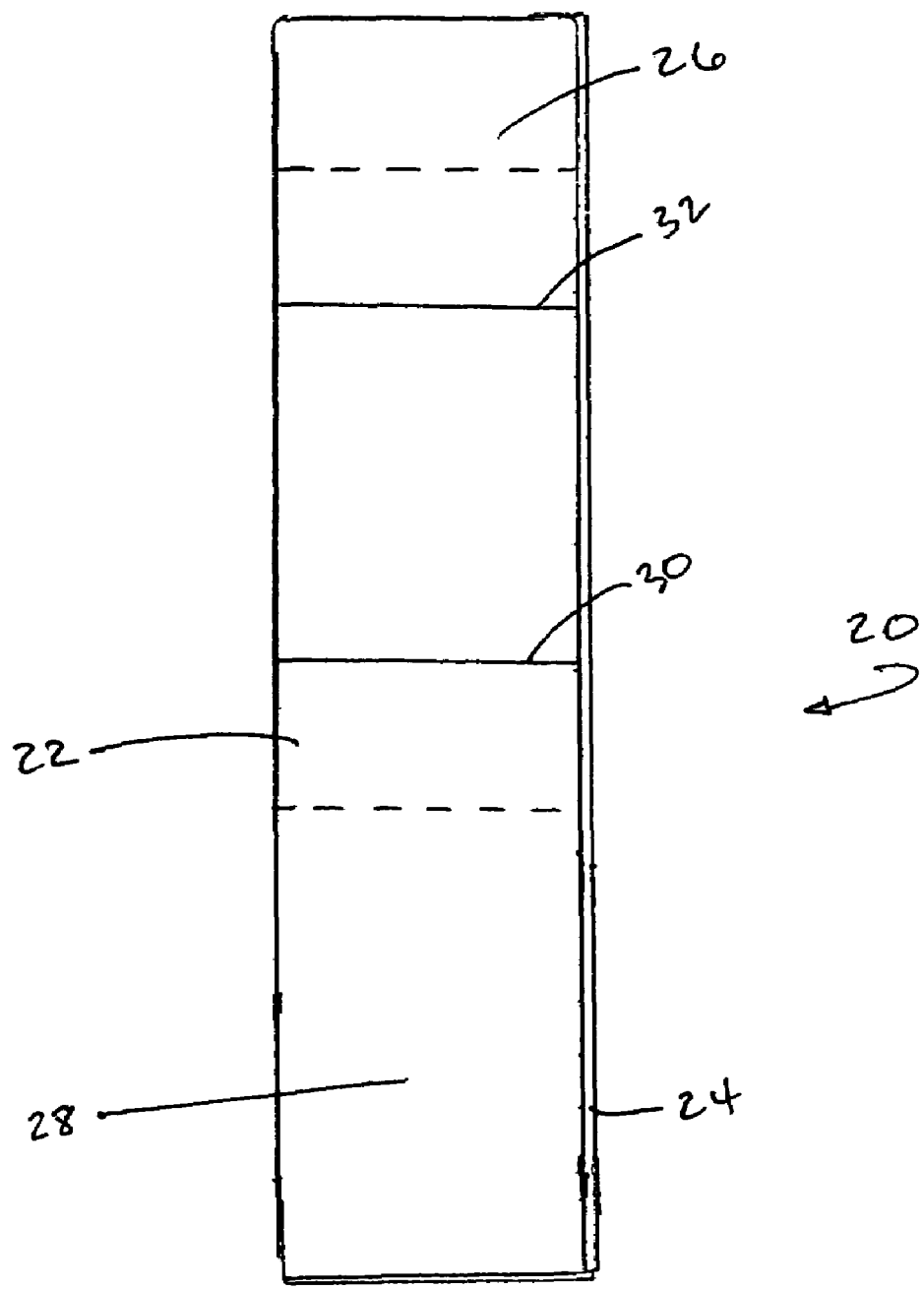
FIG. 1 is a perspective view of one embodiment of a lateral flow assay device of the present invention.

As used herein, the term "analyte" generally refers to a substance to be detected. For instance, analytes may include antigenic substances, haptens, antibodies, and combinations thereof. Analytes include, but are not limited to, toxins, organic compounds, proteins, peptides, microorganisms, amino acids, nucleic acids, hormones, steroids, vitamins, drugs (including those administered for therapeutic purposes as well as those administered for illicit purposes), drug intermediaries or byproducts, bacteria, virus particles, yeasts, fungi, protozoa, and metabolites of or antibodies to any of the above substances. Specific examples of some analytes include ferritin; creatinine kinase MB (CK-MB); digoxin; phenytoin; phenobarbitol; carbamazepine; vancomycin; gentamycin; theophylline; valproic acid; quinidine; luteinizing hormone (LH); follicle stimulating hormone (FSH); estradiol, progesterone; C-reactive protein; lipocalins; IgE antibodies; cytokines; vitamin B2 micro-globulin; glycated hemoglobin (Gly. Hb); cortisol; digitoxin; N-acetylprocainamide (NAPA); procainamide; antibodies to rubella, such as rubella-IgG and rubella IgM; antibodies to toxoplasmosis, such as toxoplasmosis IgG (Toxo-IgG) and toxoplasmosis IgM (Toxo-IgM); testosterone; salicylates; acetaminophen; hepatitis B virus surface antigen (HBsAg); antibodies to hepatitis B core antigen, such as anti-hepatitis B core antigen IgG and IgM (Anti-HBC); human immune deficiency virus 1 and 2 (HIV 1 and 2); human T-cell leukemia virus 1 and 2 (HTLV); hepatitis B e antigen (HBeAg); antibodies to hepatitis B e antigen (Anti-HBe); influenza virus; thyroid stimulating hormone (TSH); thyroxine (T4); total triiodothyronine (Total T3); free triiodothyronine (Free T3); carcinoembryoic antigen (CEA); lipoproteins, cholesterol, and triglycerides; and alpha fetoprotein (AFP). Drugs of abuse and controlled substances include, but are not intended to be limited to, amphetamine; methamphetamine; barbiturates, such as amobarbital, secobarbital, pentobarbital, phenobarbital, and barbital; benzodiazepines, such as librium and valium; cannabinoids, such as hashish and marijuana; cocaine; fentanyl; LSD; methaqualone; opiates, such as heroin, morphine, codeine, hydromorphone, hydrocodone, methadone, oxycodone, oxymorphone and opium; phencyclidine; and propoxyhene. Other potential analytes may be described in U.S. Pat. No. 6,436,651.

As used herein, the term "test sample" generally refers to a material suspected of containing the analyte. The test sample may, for instance, include materials obtained directly from a source, as well as materials pretreated using techniques, such as, but not limited to, filtration, precipitation, dilution, distillation, mixing, concentration, inactivation of interfering components, the addition of reagents, lysing, and so forth. The test sample may be derived from a biological source, such as a physiological fluid, including, blood, interstitial fluid, saliva, ocular lens fluid, cerebral spinal fluid, sweat, urine, milk, ascites fluid, mucous, synovial fluid, peritoneal fluid, vaginal fluid, amniotic fluid or the like. Besides physiological fluids, other liquid samples may be used, such as water, food products, and so forth. In addition, a solid material suspected of containing the analyte may also be used as the test sample.

In general, the present invention is directed to a lateral flow assay device for detecting the presence or quantity of an analyte residing in a test sample.

In conventional lateral flow methods, the sample is typically applied upstream from the location of the immobilized conjugate particles, such that the sample can help re-suspend the particles to allow the test to proceed. In contrast, however, the instant invention does not use immobilized conjugate particles but uses reactive chemistry to indicate the presence of the analyte. The inventive assay device includes a bibulous membrane in which a plurality of zones of a chromophore, specific to an analyte trigger which can be the analyte itself or a secondary trigger or a reaction product from the analyte and a trigger generating reagent(s), are immobilized in a precise pattern.

Reactive chemistry refers to the chemical reaction between a chromophore and an analyte. A myriad of chromophores may be chosen from depending on the specific analyte desired to be detected and the specific visual signal desired to be shown.

Desirably, chromophores in different zones can react with the trigger with the same reaction mechanisms while producing different colors. Preferably, such color change chromophores are from the same dye family while producing different colors because of their variations of their structures and functionalities.

One class of chromophore that is particularly useful in the present invention is arylmethane dyes, such as diarylmethanes, triarylmethanes, and so forth.

Triarylmethane dyes, for example, may have the following general structure:

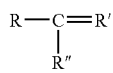

wherein R, R', and R" are independently selected from substituted and unsubstituted aryl groups, such as phenyl, naphthyl, anthracenyl, etc. The aryl groups may, for example, be substituted with functional groups, such as amino, hydroxyl, carbonyl, carboxyl, sulfonic, alkyl, and/or other known functional groups.

A common detection procedure for medical diagnostics (including glucose) involves conversion of an analyte to hydrogen peroxide prior to detection. This procedure is known in the art and is taught, for example, in U.S. Pat. No. 4,973,549. In general, peroxide will be generated as a by-product from the coupled enzymatic reactions of cholesterol esterase and cholesterol oxidase. The reaction concoction should include all appropriate enzymes, cofactors, substrates, or other additives necessary to provide a reaction with the analyte to produce a detectable amount of peroxide. In the case of cholesterol, for example, the concentration of cholesterol esterase and cholesterol oxidase will generally range from about 0.1 to 100 IU (international units) each, more usually from about 0.5 to 10 IU each. The amount of triarylmethene indicator (e.g., leucocrystal violet) should in general fall within the range of 100 pmol to 1000 pmol, but generally about 250 pmol, with sufficient non-rate-limiting amounts of catalyst such as horseradish peroxides, hemin, hemoglobin, or cytochrome C. Additionally, sufficient substrates and cofactors should be provided so as not to be rate limiting. Generally, the concentrations of the individual components will not exceed about 1 molar, usually not exceeding 0.5 molar. Buffers should normally be present having a pH in the range of about 6 to 10, usually 6.5 to 9, generally being at concentrations of about 50 to 500 mmol. Various buffers may be used including but not limited to Tris, phosphate, carbonate, and MOPS (4-morpholinepropanesulfonic acid). The particular buffer used should be chosen to minimize adverse affects imparted by the buffer. Other additives may include salt to attain a desired ionic strength, stabilizers, biocides, and solubilizations agents such as detergents and bile salts and their derivatives.

One suitable dye example is the leuco crystal violet dye family, as shown below, which includes crystal violet, malachite green, basic fuchsin and cresol red. This class of dyes can change colors upon undergoing a redox process involving an oxidant trigger such as hydrogen peroxide. This color change reaction can be greatly accelerated when the reaction is performed by employing an enzyme catalyst such as hydrogen peroxide oxidase (HRP), cytochrome C, and etc. As discussed above, the hydrogen peroxide trigger can be generated in a trigger generation zone when the sample flows from a sample application zone and through the trigger generation zone.

Leucocrystal violet in the presence of hydrogen peroxide and a catalyst produce an observable signal on nicrocellulose. The end product, crystal violet, belongs to a class of cationic triarylmethane dyes which possesses an affinity for both cellulosic and proteinaceous materials, so that much of the dye will remain fixed in place and not be easily removed. This property has been exploited by the US Federal Bureau of Investigation (FBI), for example, for the enhancement of footwear and fingerprint impression evidence. This property is important since lateral flow devices operate on a common principal; capillary flow of a mobile phase (e.g., the body fluid to be tested) through a porous solid support membrane. It is thus desired that once the indicator is placed onto the support that it not partition into, nor be carried along with, the mobile phase, which would degrade its signal. The indicator leucocrystal violet (LCV) possesses this property and is colorless, further enhancing its desirability.

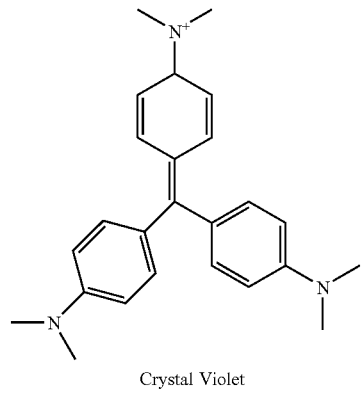

Crystal Violet

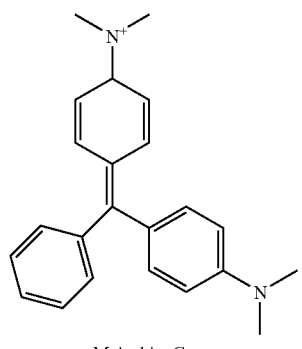

Malachite Green

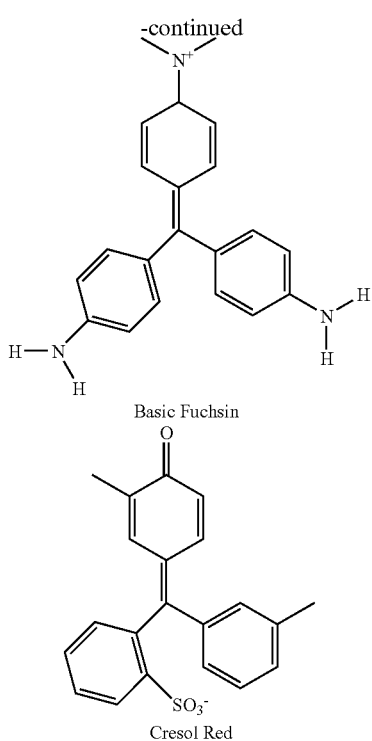

Basic Fuchsin

Cresol Red

Scavenging zones may be interspersed between reactive zones if desired. These scavenging zones contain reactants that react with the trigger but produce no visual change or produce a visual change that may be blocked physically, thereby effectively attenuating the amount of trigger in the sample.

A number of materials can be selected for scavenging purposes, depending upon the nature of the analyte. For example, in the case of cholesterol detection, the scavenging zones must be able to consume excess hydrogen peroxide between two detection zones in order to make an accurate detection at each zone. Suitable materials for this purpose include hydrogen peroxide decomposition catalysts and activated metal centers having instant hydrogen peroxide complexation properties.

The scavenger zone should be colorless, however, a chromophore may be used provided that the scavenger zones are masked from the view of the user, or that the indicator used flows with the mobile phase. Amplex red, for example, a known hydrogen peroxide indicator, possesses little affinity for nitrocellulose. Thus, striping this material between detection zones onto nitrocellulose produces a mobile scavenging zone that will not be visible once the test is complete. As excess hydrogen peroxide is being scavenged by amplex red, a fluorescent red color is produced which migrates with the solvent front leaving the originally striped area free of color.

Examples of hydrogen peroxide decomposition catalysts can be selected from low oxidation states metal oxides such as manganese oxide MnO, CoO, and NiO. Mixed metal hydroxides and metal oxides, such as those taught in U.S. Pat. No. 6,350,543 assigned to Kimberly-Clark, are also suitable for the present invention.

Metal oxides can be applied on top of the membrane strip at desired scavenging zones by an ink formulation or a paste. Examples of hydrogen peroxide scavenging or decomposition metal complexes may be selected from a number of organometallic compounds described in the literature that are known to react with hydrogen peroxide. One specific example of this type of complex can be found in A. F. M. Mokhlesur Rahman et al. (Inorganic Chemistry, 2004, 43(24), 7558-7560) and the structure of the complex is shown below:

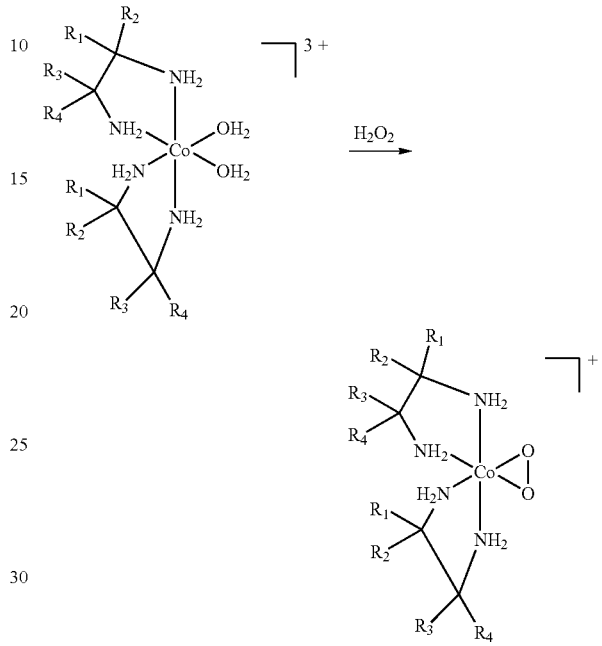

in which $R_1$ to $R_4$ are alkyl groups such as methyl and ethyl groups.

In one aspect, the use of scavenging zones between detection zones correlate to the total amount of the analyte in the sample. Ideally, the total amount of scavenging reagents in scavenging zones should be less than the total amount of analyte but equivalent to the amount from the total amount of analyte minus the total amount of dyes in the detection zones. In another aspect, the loading in different detection zones can be the same or different, depending upon the detection zone's sensitivity.

In one embodiment, the invention is a lateral flow device for cholesterol possessing five reaction zones. The first, third, and fifth zone correspond to the current medical guidelines of less than 200, 200-239, and greater than 240 mg/dL total cholesterol. Each of these zones is designed to be an all or none response; that is, they will only indicate if cholesterol or a derivative (peroxide is the most convenient choice as it is a byproduct of cholesterol oxidase catalysis) thereof penetrates the zone. The second and fourth reaction zones are designed to destroy excess cholesterol or derivative thereof.

Assuming, for example, that a sample containing 250 mg/dL cholesterol is applied to the device and converted to peroxide as discussed above, the peroxide then travels through the lateral flow membrane until it reaches zone one, indicating less than 200 mg/dl. At this point, zone one will turn green and the excess peroxide will enter zone two, a scavenging zone. The peroxide will be scavenged such that only the amount greater than 200 mg/dL cholesterol enters zone three. When the peroxide enters zone three it turns yellow, indicating cholesterol between 200 and 239 mg/dl. In zone four, another scavenging zone, peroxide corresponding to 200 to 239 mg/dL cholesterol is scavenged. Finally, as the sample enters zone five, the detection zone turns red, indicating cholesterol greater than 240 mg/dl. The overall result for the 250 mg/dL case, therefore, is the appearance of three bands; green, yellow, and red.

The device generally utilizes a porous membrane having a sample application zone and a detection zone. An optional trigger generation zone may be present, depending on the analyte to be detected.

The detection zone has chromophores specific to the analyte to be tested. The sample application zone is located on an end of the device upstream of the chromophores. The trigger generation zone is between the sample application zone and the detection zone. A wicking pad is in liquid communication with the opposite end of the porous membrane from the sample application zone on the downstream end of the device. In use, the sample is applied in the sample application zone and after a period of time, moves in the direction of the detection zone due to the capillarity of the wicking pad.

The device may optionally include scavenging zones interspersed with the control zones. The purpose of the scavenging zones is to attenuate the amount of analyte in the sample. Suitable scavenging zone reactants will depend on the analyte being tested but should be capable of reacting with the analyte without producing a visually observable signal.

The detection zone dyes and scavenging zone materials can be applied to the porous membranes simultaneously or separately. For the former, chemicals can be applied by employing a stripper or a printer. For the latter, detection zones and scavenging zones can be produced separately and then laminated together after reagents have been applied. A separate detection zone pad or scavenging zone pad can be made, for example, from a number of membrane materials such as fibrous materials, nylon membranes, nitrocellulose membranes, mech membranes, cellulose papers, and the like.

Regardless of the dyes and materials selected, any of a variety of techniques may be employed to apply them to the porous membrane. They may be applied directly to the membrane or first formed into a solution prior to application. Various solvents may be utilized to form the solution, such as, but not limited to, acetonitrile, dimethylsulfoxide (DMSO), methanol, ethanol, dimethylformamide (DMF), and other polar organic solvents. The amount of the chemical dye in the solution may range from about 0.001 to about 1 milligram per milliliter of solvent, and in some embodiments, from about 0.01 to about 0.1 milligrams per milliliter of solvent. The solution(s) may be coated onto the porous membrane using well-known techniques and then dried.

In one embodiment, a scavenging pad may be laminated between two detection zones. In order to facilitate the flow passing through the laminated scavenging pad, a channel can be created between two detection zones. For example, this channel can be created by physically scratching off the membrane or using a solvent to dissolve the membrane material (for example, using methanol alcohol to dissolve nitrocellulose membrane) between the detection zones.

Referring to FIG. 1, one embodiment of a lateral flow assay device 20 that may be formed will be described in more detail. It should be noted that the term "lateral flow" is meant to be descriptive and not limiting, as the device could be configured in other ways with the same effect. Radial or vertical flow devices can easily be envisioned, for example, employing the same principle as the instant invention, without departure from the spirit of the invention. As shown, the device 20 contains a porous membrane 22 optionally supported by a rigid material 24. The porous membrane 22 has a detection zone (or line) 30.

In general, the porous membrane 22 may be made from any of a variety of materials through which the detection probes are capable of passing. For example, the materials used to form the porous membrane 22 may include, but are not limited to, natural, synthetic, or naturally occurring materials that are synthetically modified, such as polysaccharides (e.g., cellulose materials such as paper and cellulose derivatives, such as cellulose acetate and nitrocellulose); polyether sulfone; polyethylene; nylon; polyvinylidene fluoride (PVDF); polyester; polypropylene; silica; inorganic materials, such as deactivated alumina, diatomaceous earth, $MgSO_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon or rayon); porous gels, such as silica gel, agarose, dextran, and gelatin; polymeric films, such as polyacrylamide; and the like. In one particular embodiment, the porous membrane 22 is formed from nitrocellulose and/or polyether sulfone materials. It should be understood that the term "nitrocellulose" refers to nitric acid esters of cellulose, which may be nitrocellulose alone, or a mixed ester of nitric acid and other acids, such as aliphatic carboxylic acids having from 1 to 7 carbon atoms. Suitable membranes include nitrocellulose membranes HF075 and HF120 from Millipore Corporation of Billerica, Mass., USA.

The device 20 may also contain a wicking pad 26. The wicking pad 26 generally receives fluid that has migrated through the entire porous membrane 22. As is well known in the art, the wicking pad 26 may assist in promoting capillary action and fluid flow through the membrane 22.

To initiate the detection of an analyte within the test sample, a user may directly apply, contact or deposit the test sample to an application zone 28. The sample travels through the porous membrane 22, to the detection zone 30 and a visual signal is seen if the desired analyte is present.

Referring again to FIG. 1, the assay device 20 contains a detection zone 30 within which is immobilized a first chromophore that is capable of chemically reacting with the analyte. The binding of the analyte results in a detectible indication that the analyte is present and such an indication is visual. The analyte containing sample may continue to move forward in the device until it reaches a second chromophore in a second detection zone 32, which again results in a visually detectable color change. The detection zones may generally provide any number of distinct detection regions so that a user may better determine the concentration of a particular analyte within a test sample. Each region may contain the same chromophores, or may contain different chromophores for capturing multiple analytes. For example, the detection zone 30 may include two or more distinct detection regions (e.g., lines, dots, etc.). The detection regions may be disposed in the form of lines in a direction that is substantially perpendicular to the flow of the test sample through the assay device 20. Likewise, in some embodiments, the detection regions may be disposed in the form of lines in a direction that is substantially parallel to the flow of the test sample through the assay device.

Figure 2:
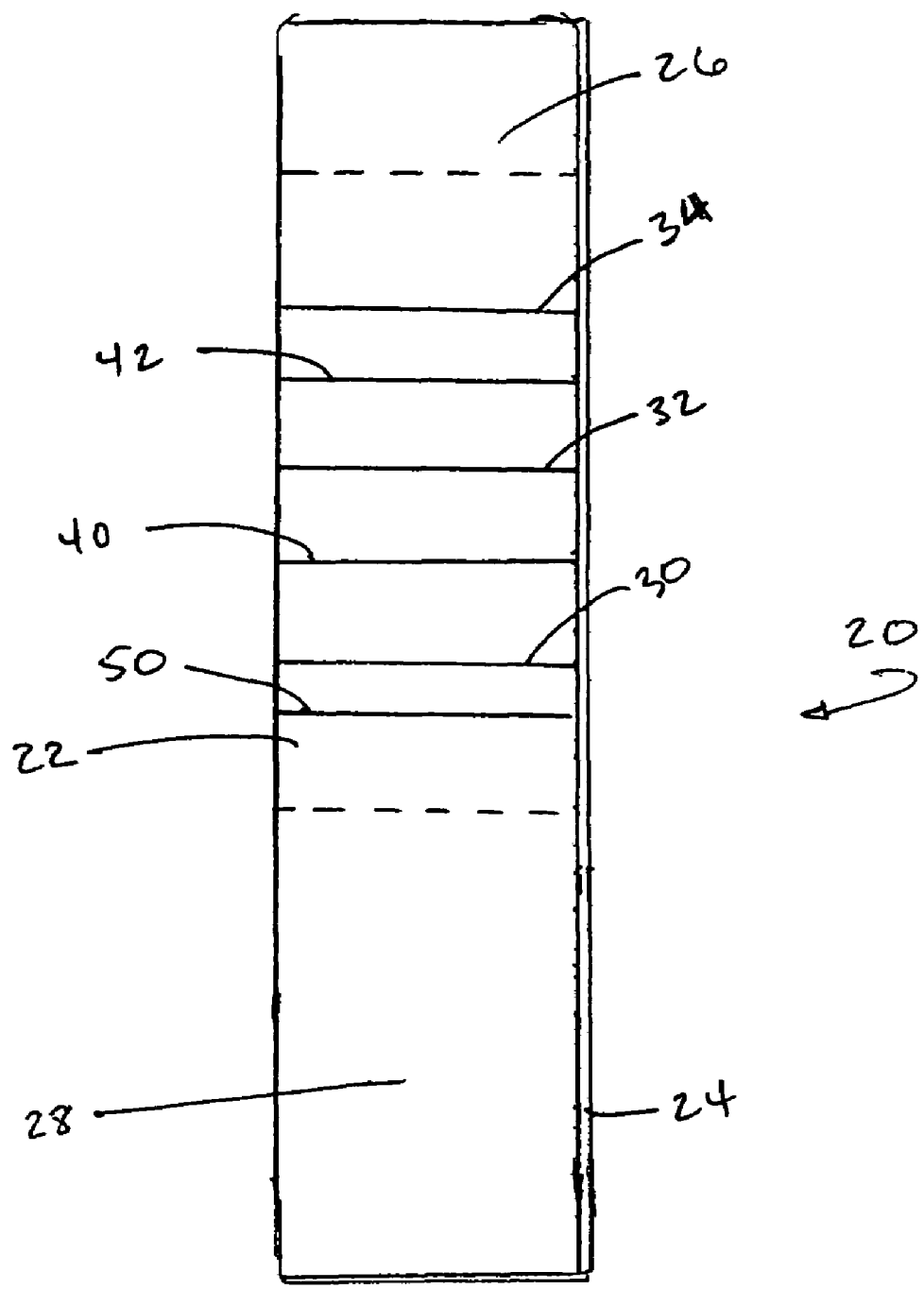
FIG. 2 is a perspective view of one embodiment of a lateral flow assay device of the present invention containing scavenging zones.

Referring to FIG. 2, an embodiment including scavenging zones is shown. The scavenging zones 40, 42 are located between the detection zones 30, 32, 34. This embodiment also includes a trigger generation zone 50 between the sample application zone 28 and the first detection zone 32.

One embodiment of this invention is detailed as follows for the construction of a two zone hydrogen peroxide sensor.

EXAMPLE 1

A twenty five millimeter wide by 30 centimeter long strip of nitrocellulose (Millipore Corp., SHF1200425) was laminated to a 25 mm wide area of a 60 mm by 30 cm Millipore backer card (HF000MC100) leaving 15 mm of the backer card exposed on one side of the nitrocellulose strip and the balance (20 mm) on the other side. A leucocrystal violet (LCV, Hiton-Davis Chemical Co., Cincinnati, Ohio) indicator solution was prepared by mixing a solution of 1.4 mM LCV in 0.5% hydrochloric acid with one milliliter of 1.4 mg/mL of horse liver cytochrome C (Sigma-Aldrich Corp, St. Louis, Mo.). The resulting solution equilibrated for one hour at room temperature prior to use. Next, HPLC grade methanol (Sigma-Aldrich Corp.) was added to the blend until a final concentration of three percent LCV by volume was achieved. The LCV solution was jetted onto the aforementioned nitrocellulose using a Kinematic Automation (Twain Harte, Calif.) Matrix 1600 reagent distribution system equipped with dual non-contact spray heads (jetting parameters of 0.9 uL dye/cm and a striping rate of 7 cm/sec). The stripes were located approximately ten and fifteen millimeters from the bottom edge of the nitrocellulose membrane. Next, a glass fibre/cellulose mix wicking pad (CF6, Whatman, Clifton, N.J.) was applied to the exposed 15 mm wide area of the backer card such that a 1 to 1.5 mm overlap with the bibulous nitrocellulose membrane was attained. The card was dried at 37° C. for one hour in a zero humidity environment. After drying, the un-laminated part of the backer card, i.e., about 20 mm, was removed using a pair of scissors, and discarded. Finally, the (now) approximately 40 mm wide by 30 cm long laminated card was cut into four millimeter wide strips (Kinematic Automation Matrix 2360 programmable shear) and placed into a plastic bag containing a desiccant pouch (MiniPax®, Multisorb Technologies, Inc., Buffalo, N.Y.) so that it would remain moisture-free. It should be noted that each reaction zone contains 250 picomoles of LCV which is known to react in the presence of a catalyst in a 1:1 stochiometry. Thus, the first detection zone is triggered when a test solution contains hydrogen peroxide; however, the second detection zone LCV stripe is triggered only if the solution contains more than 250 picomoles of hydrogen peroxide.

To test the device, all reactions were carried out at room temperature under ambient room conditions as follows:

Twelve two fold serial dilutions of hydrogen peroxide (Component D of the Amplex Red Cholesterol Assay Kit, A12216, Molecular Probes Inc., Eugene, Oreg.) in 100 mM sodium phosphate buffer, pH 5.88 reaction buffer were prepared. Next, One microliter of each of the resulting solutions was pipetted three millimeters from the bottom edge of twelve test strips. The tests were initiated by placing a strip into forty microliters of 100 mM sodium phosphate buffer, pH 5.88. The reactions proceeded unhindered until all the buffer had been absorbed by the test strip, taking approximately five minutes.

The conversion of LCV to crystal violet was quantified using a Hewlett Packard ScanJet 5470C digital scanner. Briefly, the scanner was set to grayscale mode at 1200 DPI using the factory default exposure settings. Scanned data were saved as uncompressed tagged image format files (TIFF) which were subsequently opened within Adobe Photoshop CS and converted to grayscale. Although the data was collected as a grayscale image, a bit flag in the TIFF file prevented it from being directly imported into the quantization software package. Next, the grayscale values were inverted due to the inversion that occurs automatically when imported into Image Quant 5.2 (Amersham Biosciences, Piscataway, N.J.), the image analysis software used for quantization. This effectively preserved each file's original content. Next, the file was imported into Image Quant version 5.2, and a rectangular region of interest (ROI) was created within the software containing the developed band. An exact duplicate of this ROI was created for each remaining band as well as one for the background. It should be noted that random measurements of different areas of the undeveloped membrane were within three percent of each other (data not shown), thus the location for the background ROI was chosen to lie between the two stripes. The software then calculated the volume (sum of the individual pixel intensities over the entire ROI) for each region. Each ROI was corrected by subtracting the background ROI value from each stripe. Each stripe's data was plotted as a function of relative hydrogen peroxide concentration using a value of 100 for the highest peroxide solution.

Unexpectedly and irrespective of the concentration of hydrogen peroxide, both reaction zones changed color to the same extent. For this to occur, either the reaction dynamics must be too slow to efficiently capture the hydrogen peroxide as it passes through a striped indicator zone, or the peroxide solution is traveling around the bands. To assess the latter possibility, we spiked one milliliter of reaction buffer with one drop of green food dye (McCormick & Company, Inc., Sparks, Md.). Next, a lateral flow strip was affixed to the stage of a Digital Blue QX5 Computer Microscope (Digital Blue, Hayward, Calif.). The microscope was set to collect digital video at 640×480 pixels resolution and 15 frames per second. After initiating data collection, ten microliters of the green dye solution was applied to the bottom edge of the nitrocellulose using a common laboratory pipette.

Video was collected until the nitrocellulose matrix was saturated with green dye. When the video footage was reviewed, it was discovered that prior to the first LCV zone, the solvent front was nearly flat across the entire membrane. Initial stripe penetration induced little change in the front. When the striped area is nearly one third wet, however, the outer edges of the solvent start migrating up the edges of the nitrocellulose strip faster than through the center, creating a U-shaped solvent front. Stripe wetting further slows but the reaction buffer continues moving up the edges until it reaches the end of the band. At this point, lateral migration above the band continues toward the center of the strip. After the now laterally migrating edge fronts meet in the center of the strip above the first reaction zone, wetting continues in both an upward and downward fashion. Thus, the first reaction zone is partially wetted, encapsulated, and then finally fully wet from the top down. The second reaction zone has an identical fate.

This phenomenon is well known in the lateral flow literature and has been dubbed "submarining". Generally, this results from vastly different membrane surface energies. In this case, the dried dye produces a hydrophobic patch that is vastly different than the rest of the membrane. To compensate for this issue, surface energy matching must occur and is most commonly accomplished via a post blocking step using any number of techniques commonly known in the art. Further information regarding troubleshooting nitrocellulose membranes may be found at http://www.devicelink.com/ivdt/archive/99/05/002.html.

One with experience in the art can alleviate the problem of submarining by optimizing the striping conditions. Additionally, the concentration of the catalyst may need to be optimized to facilitate efficient capture and catalysis of hydrogen peroxide within the indicator zones using any number of techniques commonly used in the art culminating in a test in which a particular, predefined dose of hydrogen (based on the concentration of LCV within the reaction zone) induces a color change in only the bottom LCV stripe.

EXAMPLE 2

A Whatman Filter paper (CAT No. 1003110, cut to size 31.75×31.75 mm) was first soaked with 0.1 g/ml Hybrane-32 dendrimer (DSM Corporation) for about three minutes and then by 15 ml of 13.3 mg/ml $FeCl_2$ aqueous solution for three minutes. The resulted yellowish filter paper was then thoroughly washed with water and then dried at 37° C. The dried filter paper was next cut into 3×4 mm scavenging pads for hydrogen peroxide scavenging.

To demonstrate the hydrogen peroxide scavenging between two chromophore bands, a strip with two chromophore bands and one scavenging band was assembled using test strips identical to those produced in Example 1.

A 3 by 4 mm scavenging pad was placed on top of the channel between the two chromophore bands, held in by tape, and the tests were initiated by placing the end of a strip into forty microliters of 100 mM sodium phosphate buffer (pH 5.88) that contained 2 microliters of 25 mM hydrogen peroxide solution. The intense color change was observed for the first band and the second band only showed a faint color change. Under the same conditions, a control scavenging pad without scavenging reagents led to intense color changes for both chromophore bands.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A lateral flow assay device for detecting the presence or quantity of an analyte residing in a test sample, said lateral flow assay device comprising a porous membrane, said porous membrane being in communication with a wicking pad, said porous membrane defining in order:
    a sample application zone where a sample containing an analyte is deposited;
    a trigger generation zone in which said analyte reacts with a material to produce hydrogen peroxide;
    a first detection zone within which is immobilized a first chromophore, said first chromophore being configured to react chemically with hydrogen peroxide to generate a visually detectible signal;
    a first scavenging zone having a first scavenging material configured to react chemically with hydrogen peroxide without generating a visually detectible signal;
    a second detection zone within which is immobilized a second chromophore, said second chromophore being configured to react chemically with hydrogen peroxide to generate a visually detectible signal;
    a second scavenging zone having a second scavenging material configured to react chemically with hydrogen peroxide without generating a visually detectible signal; and,
    a third detection zone within which is immobilized a third chromophore, said third chromophore being configured to react chemically with hydrogen peroxide to generate a visually detectible signal.

2. The assay device as defined in claim 1, wherein said chromophore is an arylmethane.

3. The assay device as defined in claim 2, wherein said arylmethane is selected from the group consisting of diarylmethanes and triarylmethanes.

4. The assay device as defined in claim 2, wherein said chromophore is a triarylmethane having the following general structure:

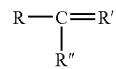

wherein R, R', and R" are independently selected from substituted and unsubstituted aryl groups.

5. The assay device as defined in claim 4, wherein at least one of said aryl groups is amino-substituted, hydroxyl-substituted, carboxyl-substituted, sulfonic-substituted, alkyl-substituted, carbonyl-substituted, or combinations thereof.

* * * * *